United States Patent [19]

Novick, Jr.

[11] Patent Number: 5,039,666
[45] Date of Patent: Aug. 13, 1991

[54] AMINOGLYCOSIDE COMPOSITION HAVING SUBSTANTIALLY REDUCED NEPHROTOXICITY INDUCED BY THE AMINOGLYCOSIDE

[75] Inventor: William J. Novick, Jr., Lebanon, N.J.

[73] Assignee: Hoechst-Roussel Pharmaceuticals Inc., Somerville, N.J.

[21] Appl. No.: 606,018

[22] Filed: Oct. 30, 1990

[51] Int. Cl.$^5$ .............................................. A61V 31/70
[52] U.S. Cl. ......................................... 517/37; 514/39
[58] Field of Search ..................................... 514/37, 39

[56] References Cited

U.S. PATENT DOCUMENTS

| 4,002,742 | 1/1977 | Wright et al. | 424/180 |
| 4,029,882 | 6/1977 | Wright | 536/17 |
| 4,235,892 | 11/1980 | Nagabhushan | 424/228 |

Primary Examiner—Stanley J. Friedman
Attorney, Agent, or Firm—Jerome Rosenstock; Raymond R. Wittekind

[57] ABSTRACT

This invention relates to an aminoglycoside composition having reduced nephrotoxicity induced by the aminoglycoside which comprises a selected aminoglycoside and a compound present in an effective amount selected from the group consisting of (a) at least one 7-(oxoalkyl)1,3-dialkyl xanthine of the formula

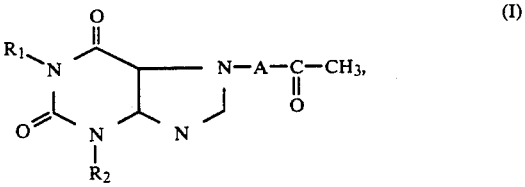

in which $R_1$ and $R_2$ are the same or different and are independently selected from the group consisting of straight-chain or branched alkyl radicals with 2 to 6 carbon atoms, cyclohexyl, straight-chain or branched chain alkoxyalkyl and hydroxyalkyl radicals; and A is a hydrocarbon radical with up to 4 carbon atoms which can be substituted by a methyl group; (b) a compound of the formula

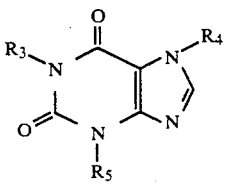

wherein at least one of $R_3$ and $R_4$ is a branched hydroxyalkyl group of the formula

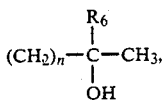

with a tertiary alcohol function, which $R_6$ stands for an alkyl group with 1 to 3 carbon atoms and n stands for a whole number from 2 to 5, the other $R_3$ or $R_4$ group that may optionally be present stands for a hydrogen atom or an aliphatic hydrocarbon group $R_7$ with up to 6 carbon atoms, whose carbon chain may be interrupted by up to 2 oxygen atoms or may be substituted with an oxo group or up to two hydroxyl groups $R_5$ is an alkyl group having 1 to 4 carbon atoms; and (c) a suitable mixture of the foregoing.

25 Claims, No Drawings

AMINOGLYCOSIDE COMPOSITION HAVING SUBSTANTIALLY REDUCED NEPHROTOXICITY INDUCED BY THE AMINOGLYCOSIDE

BACKGROUND OF THE INVENTION

Aminoglycosides, such as gentamicin, amikacin, kanamycin, neomycin, netilimicin, streptomycin, tobramycin, etc and their salts, e.g. sulfates, are well known compounds which are typically used in hosts, e.g. mammals, as therapeutic agents, such as for example as antibiotics, antibacterials, etc. It is a well known fact that aminoglycosides generally induce a nephrotoxic side reaction when used in the treatment of such hosts, e.g. mammals, such as man. This nephrotoxicity oftentimes proves fatal or at the very least limits the beneficial application of the aminoglycoside compound, e.g. as an antibiotic. An aminoglycoside composition having reduced nephrotoxicity or a method which reduces the nephrotoxic side-effect is desired and is needed.

SUMMARY OF THE INVENTION

This invention relates to an aminoglycoside composition having reduced nephrotoxicity induced by the aminoglycoside and more particularly, to such a composition comprising the aminoglycoside and a compound selected from the group consisting of (a) a suitable 7-(oxoalkyl)1,3-dialkyl xanthine of the formula

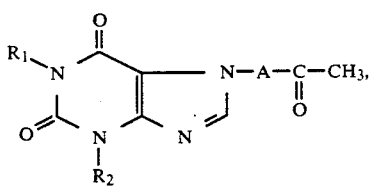

(b) a xanthine of the formula

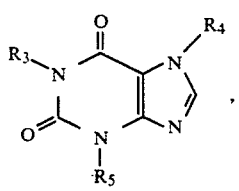

and (c) a suitable mixture of the foregoing, where $R_1$ through $R_5$ are various substituents defined hereinafter.

More particularly, this invention provides a method of inhibiting or reducing nephrotoxicity in a host, e.g. a mammal, induced by an aminoglycoside by treating the host with a compound selected from the group consisting of (a) a compound of the formula I, (b) a compound of the formula II, and (c) a suitable mixture of the foregoing compounds.

DETAILED DESCRIPTION

It is known that the administration of an aminoglycoside, such as for example (a) streptomycin; (b) netilmicin and 1-N-acyl-4,6-di(aminoglycosyl)aminocyclitols, as described in U.S. Pat. No. 4,029,882, incorporated by reference hereinto in its entirety, as well as 1-N-alkyl-4,6-di(aminoglycosyl)-1,3-diaminocyclitols of U.S. Pat. No. 4,002,742, incorporated by reference hereinto in its entirety; (c) neomycin; (d) kanamycin, (also known as kanamycin A), kanamycin B and kanamycin C; (e) gentamicin, including gentamicins $C_1$, $C_2$, $C_{1a}$ and gentamicin A; (f) tobramycin or nebramycin, including nebramycin II, IV, V and VI as described in U.S. Pat. No. 3,691,279, incorporated by reference hereinto in its entirety; and (f) amikacin and 1-[L-(−)-Y-amino-α-hydroxybutyryl]-kanamicin A and B as described in U.S. Pat. No. 3,781,268, incorporated hereinto by reference in its entirety, and the pharmaceutically acceptable salts of any of the foregoing, e.g. sulfate, to a host, e.g. mammal, induces nephrotoxicity with acute renal failure in such treated host. It has been discovered that combining any aminoglycoside, which induces such nephrotoxicity in the host, e.g. mammal, being treated, with a selected suitable xanthine or treating the aminoglycoside treated mammal with such suitable xanthine results in inhibiting or substantially reducing the induced nephrotoxicity. A suitable xanthine is one having the formula

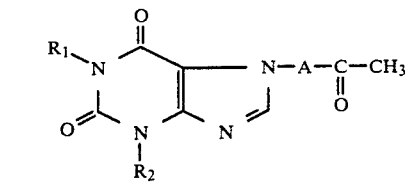

The substituents $R_1$ and $R_2$ in formula (I) are the same or different and are independently selected from the group consisting of straight-chain or branched alkyl radicals with 2 to 6 carbon atoms, cyclohexyl, straight-chain or branched chain alkoxyalkyl and hydroxyalkyl radicals. The substituent A represents a hydrocarbon radical with up to 4 carbon atoms which can be substituted by a methyl group. One suitable compound of Compound I is 1,3-di-n-butyl 7-(2-oxopropyl)xanthine. This compound, which is also referred to herein in abbreviated form as "DBOPX", has the following formula:

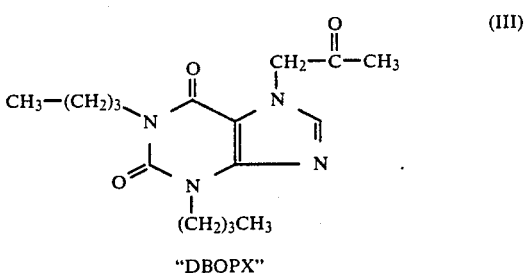

"DBOPX"

Inhibition or reduction of the nephrotoxic induced effect of a selected aminoglycoside can also be achieved with a second suitable xanthine of the formula

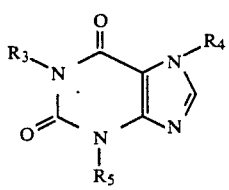

wherein at least one of $R_3$ and $R_4$ is a branched hydroxyalkyl group of the formula

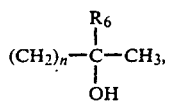

with a tertiary alcohol function, in which $R_6$ stands for an alkyl group with 1 to 3 carbon atoms and n stands for a whole number from 2 to 5, the other $R_3$ or $R_4$ group that may optionally be present stands for a hydrogen atom or an aliphatic hydrocarbon group $R_7$ with up to 6 carbon atoms, whose carbon chain may be interrupted by up to 2 oxygen atoms or may be substituted with an oxo group or up to two hydroxyl groups and $R_5$ is an alkyl group having 1 to 4 carbon atoms.

Compound II can be combined with the selected aminoglycoside to form a therapeutic composition or Compound II can be separately administered to the host or patient to be treated.

Exemplary within the general formula II in inhibiting or reducing aminoglycoside induced nephrotoxicity is the compound of the formula

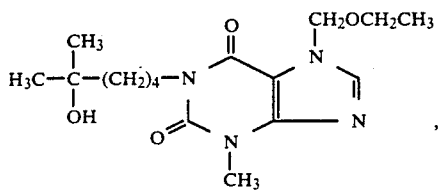

which is hereinafter designated "HWA448", and the compound of the formula

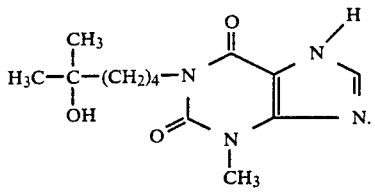

Some other compounds within the general formula II are those identified by their R substituents as set forth below:

| COMPOUND OF FORMULA (II) | | |
| --- | --- | --- |
| $R_3$ | $R_5$ | $R_4$ |
| $CH_3-\overset{O}{\underset{\|}{C}}-(CH_2)_4-$ | $-CH_3$ | $-CH_2-CH_2-CH_3$ |
| $CH_3-\overset{OH}{\underset{\underset{CH_3}{\|}}{C}}-(CH_2)_4-$ | $-CH_3$ | $-CH_2-CH_2-O-CH_3$ |
| " | " | $-CH_2-O-(CH_2)_2-O-CH_3$ |
| " | " | $-CH_2-CH_2-CH_3$ |
| " | " | $-CH_2-\overset{OH}{\underset{\|}{CH}}-CH_3$ |
| " | " | $-CH_2-\overset{OH}{\underset{\|}{CH}}-(CH_3)_2$ |
| " | $-CH_2-CH_3$ | $-CH_2-O-CH_2-CH_3$ |
| " | $-CH_3$ | $-(CH_2)_4-\overset{CH_3}{\underset{\underset{OH}{\|}}{C}}-CH_3$ |
| " | " | $-CH_2-O-CH_2-CH_3$ |

The xanthine or mixture of xanthines selected from Compounds I and II is employed in an amount that is effective in inhibiting or reducing the nephrotoxic effect or nephrotoxicity which is induced by an aminoglycoside exhibiting such inducing quality.

The compounds employed in this invention will now be described in more detail, and methods for preparing the compounds will be provided.

The subject invention utilizes 7-(oxoalkyl) 1,3-dialkyl xanthines of formula (I) above. While DBOPX is one such xanthine, a number of other compounds, such as 7-(3-oxobutyl)-1,3-di-n-butyl xanthine can be employed. For example, the xanthines of formula (I) can be substituted by other alkyl groups, or by alkoxy or hydroxyalkyl groups. Suitable alkyl groups include branched and straight chain groups, such as ethyl, propyl, isopropyl, butyl, sec-butyl, tert-butyl, amyl, hexyl, and the like. Alkoxy substituted alkyl groups are branched and straight chain groups containing from 2 to 6 carbon atoms in the combined alkoxy and alkyl groups, including methoxymethyl, amyloxymethyl, methoxyethyl, butoxyethyl, propoxypropyl, and the like. Hydroxyalkyl groups are those containing from 1 to 6 carbon atoms, such as hydroxymethyl, hydroxyethyl, hydroxypropyl, hydroxyhexyl, and the like.

The hydrocarbon groups represented by A in formula (I) above are divalent saturated aliphatic hydrocarbon groups, i.e., methylene, ethylene, trimethylene and tetramethylene, which can be substituted on the carbon adjacent the carbonyl group with methyl. Such methyl-substituted groups include ethylidine, 1,2-propylene and 1,3-butylene groups.

The compounds of the formula (I) employed in this invention can be synthesized using known techniques. For example, the compounds can be prepared at elevated temperature, optionally in the presence of a solvent, by reacting correspondingly substituted 1,3-dialkyl xanthines of the formula

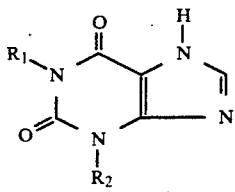

in which $R_1$ and $R_2$ are as defined above, with $\alpha,\beta$-unsaturated methyl ketones corresponding to the formula

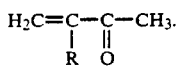

The substituent R in formula (V) represents hydrogen or a methyl group. The reaction can be conducted in an alkaline medium.

An alternative method of preparation involves reacting alkali metal salts of 1,3-dialkyl xanthine derivatives of general formula (IV), in which $R_1$ and $R_2$ are as defined above, with oxoalkyl halides corresponding to the formula

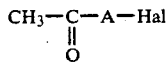

in which A is as defined above, and Hal represents a halogen atom, preferably chlorine or bromine.

These reactions are preferably carried out at temperatures in the range from 40° to 80° C., optionally under elevated or reduced pressure, but usually at atmospheric pressure. The individual starting compounds can be employed either in stoichiometric quantities or in excess. The alkali salts in the alternative method of preparation can either be prepared beforehand or in the reaction itself.

Suitable solvents for use in the reaction are water-mixcible compounds, preferably lower alcohols, such as methanol, propanol, isopropanol, and various butanols; also acetone; pyridine; triethylamine; polyhydric alcohols, such as ethylene glycol and ethylene glycol monomethyl or monoethyl ether.

The compounds of formula (I) are known for their marked effect in increasing blood flow through skeletal muscle and by their low toxicity. The most preferred of these compounds for use in accordance with the present invention is 1,3-dibutyl 7-(2-oxopropyl)xanthine, i.e. DBPOX.

A more detailed description of the compounds of formula (I) employed in this invention and methods of preparing the compounds are contained in U.S. Pat. No. 4,242,345, the entire disclosure of which is relied upon and incorporated by reference hereinto.

For the cases where at least one of $R_3/R_4$ is a tertiary alcohol reference may be had to the international application PCT-EP-86-00401, July 8, 1986, claiming German priority of July 8, 1985, and U.S. Pat. No. 4,833,146. This application and U.S. Pat. No. 4,833,146 addresses, as their invention, a variety of embodiments of synthesis routes for the xanthines of formula (II) embraced in the current invention. The entire disclosure of U.S. Pat. No. 4,833,146 is relied upon and incorporated by reference thereinto.

An example of one embodiment consists of a) reacting 3-alkylxanthines of formula (VII)

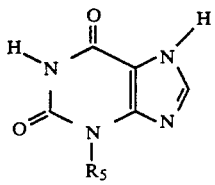

in which the $R_5$ represents alkyl with up to 4 carbon atoms, with alkylating agents of formula (VIII)

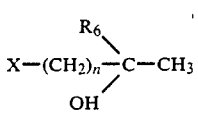

in which X stands for halogen, preferably chlorine, bromine, or iodine, or a sulfonic acid ester group or a phosphoric acid ester group and $R_6$ and n have the meanings mentioned above, to obtain compounds of formula (IX)

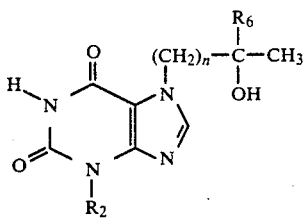

with a tertiary hydroxyalkyl group in the position of $R_4$ and hydrogen in the position of $R_3$, and $a_1$) alkylating this with the same or different alkylating agent of formula (VIII) to obtain compounds pursuant to the invention of formula (X)

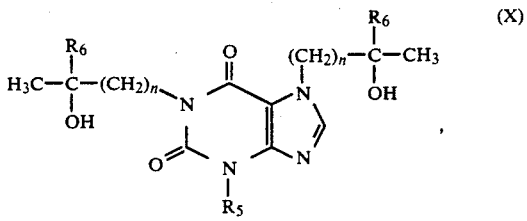

with two identical or different tertiary hydroxyalkyl groups in the positions of $R_3$ and $R_4$, or $a_2$) converting it with a compound of the formula $R_7$-X (Xa), in which X has the meaning given in formula (VIII) and $R_7$ has the meaning indicated above, into compounds of formula (XI),

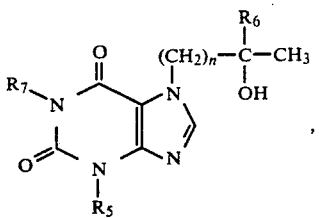

(XI)

in all cases preferably operating in the presence of basic media or using the xanthines in the form of their salts.

Another form of embodiment b) consists of substituting 1,3-dialkylated xanthines of formula (XII),

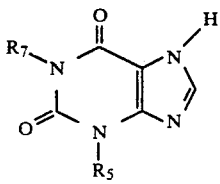

in the 7-position, preferably in the presence of basic media or in the form of their salts, by one-step reaction with a compound of formula (VIII), to obtain compounds of the formula (XI).

Another form of embodiment c) consists of first reacting the 3-alkylxanthines of formula (VII), likewise preferably in the presence of basic media or in the form of their salts, with a compound of the formula $R_{15}$-X (XIII), with the formation of 3,7-disubstituted xanthines of formula (XIV)

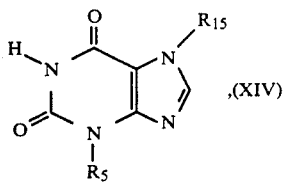

,(XIV)

in which $R_{15}$ has the meaning for $R_7$ or stands for benzyl or diphenylmethyl, and then substituting them in the 1-position, again preferably in the presence of basic media or in the form of their salts, with a compound of formula (VIII), with compounds of formula (XV)

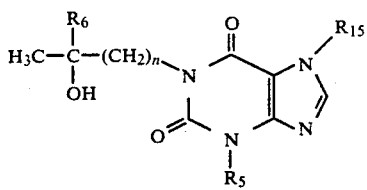

being obtained, and converting the compounds of formula (XV) in which $R_{15}$ represents a benzyl or diphenylmethyl being obtained, and converting the compounds of formula (XV) in which $R_{15}$ represents a benzyl or diphenylmethyl group or an alkoxymethyl or alkoxyalkoxymethyl group, under reducing or hydrolytic conditions, into compounds pursuant to the invention of formula (XVI)

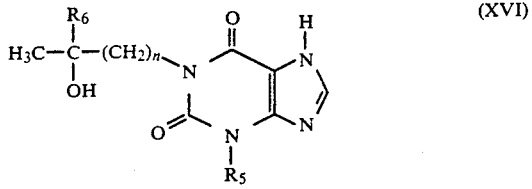

(XVI)

that are subsequently reacted again, if desired, with a compound of formula (VIII) or (Xa) to obtain compounds pursuant to the invention of formula (X) or (XV).

Another form of embodiment d) consists of reducing compounds of formula (XI) or (XV) pursuant to the invention in which $R_7$ or $R_{15}$ stands for an oxoalkyl group, with conventional reducing agents for the keto group to obtain the corresponding hydroxyalkylated xanthines pursuant to the invention.

The 3-alkyl- or 1,3-dialkylxanthines of formula (VII) or (XII) used here as starting materials and the "alkylating agents" of formulas (VIII), (Xa), and (XIII) are known for the most part or can be prepared readily by methods disclosed in the literature. Thus, the tertiary alcohols of formula (VIII), for example, can be obtained by organometallic synthesis by reacting the sterically unhindered haloketones of the formula Hal—($CH_2$)$_n$—CO—$CH_3$ (XVII) in a so-called synthetic reaction with reductive alkylation of the carbonyl group, with alkylmetal compounds $R_6$-M, especially of magnesium, zinc, or lithium, for example in the form of alkylmagnesium halides $R_6$-MgHal (Grignard compounds) or of the alkyllithium compounds $R_6$-Li under the usual conditions (for example, see Houben-Weyl, Vol. VI/I a, Part 2 (1980), pp. 928–40, especially pp. 1021 ff. and 1104–1112). In the same way, a reaction of the haloketones with the formula Hal—($CH_2$)$_n$—CO—$R_6$ (XVIII) with methylmagnesium halides or methyllithium likewise leads to the target.

The hydroxyketones corresponding to the formula (XVII) and (XVIII) can also be converted smoothly into diols with the alkylmethyl compounds in the usual way, either directly or with temporary masking of the hydroxy group, for example by acetal formation with 5,6-dihydro-4H-pyran (for example, see Houben-Weyl, Vol. VI/I a, Part 2 (1980), pp. 1113–1124), from which compounds of formula (VIII) are formed by selective esterification of the terminal primary hydroxyl groups with sulfonyl or phosphoric halides or anhydrides, advantageously in the presence of basic media.

Other possibilities for the synthesis of the tertiary alcohol derivatives of formula (VIII) consist of the monometallation of ω-chloro-1-bromoalkanes to obtain ω-chloroalkylmetal compounds, (Houben-Weyl, Vol. XIII/2 a (1973), pp. 102 and 319) and their subsequent reaction with the ketones $R_6$—CO—$CH_3$, with the extent of by-product formation from the alkanolates formed as intermediates because of their tendency toward ring closure with the elimination of metal salt being minimized by appropriate temperature control, or of using ω-halo-1-alkanols as starting materials, which are metallated in the usual way, preferably in the form of the tertiaryhydropyranyl-(2) ether or after alkanolate formation of the hydroxy group (MO—($CH_2$)$_n$—Hal) with any desired alkylmetal compound (for example, see Houben-Weyl, Vol. XIII/2 a (1973, p. 113), then reacting them with the ketones $R_6$—CO—$CH_3$ to obtain the diols mentioned in the preceding paragraph (Houben-Weyl, Vol. VI/I a, Part 2 (1980), p. 1029), and subsequently selectively esterifying the primary hydroxy group with suitable sulfonic or phosphoric acid derivatives.

A convenient access to compounds of formula (VIII) in which $R_6$ represents a methyl group is also available through the reaction of ω-haloalkanoic acid alkyl esters (Hal—$(CH_2)_n$—COO—alkyl) with two equivalents of a methylmetal compound, with the ester reacting through the ketone to produce the tertiary alcohol with the introduction of two methyl groups (Houben-Weyl, Vol. VI/I a, Part 2 (1980), pp. 1171-1174). In the same way, ω-hydroxycarboxylic acid esters can be converted into diols with methylmetal compounds with or without protection of the hydroxy group, for example in the form of tetrahydropyranyl-(2) or methoxymethyl ether, or optionally in the form of the lactones as cyclic esters (for example, see Houben-Weyl, Vol. VI/I a, Part 2 (1980), pp. 1174-1179), from which active alkylating agents of formula (VIII) can in turn be obtained by selective esterification of the primary hydroxyl group with sulfonic or phosphoric halides or anhydrides.

Suitable compounds of formula (VIII) that can be prepared by the methods described above are thus the [(ω-1)-hydroxy-(ω-1)-methyl]butyl, -pentyl, -hexyl, and -heptyl, the [(ω-2)-hydroxy-(ω-2)-methyl]pentyl, -hexyl, -heptyl, and -octyl, and the [(ω-3)-hydroxy-(ω-3)-methyl]hexyl, -heptyl, -octyl, and -nonyl chlorides, bromides, iodides, sulfonates, and phosphates.

Among the compounds of formula $R_7$-X (xa) or $R_{15}$-X (XIII) suitable for the introduction of $R_7$ into the 1- or 7-position and of $R_{15}$ into the 7-position of the xanthine skeleton, the alkoxymethyl and alkoxyalkoxymethyl derivatives occupy a special position as their halides can indeed be used successfully as reactants but toxicological problems can arise, at least in largescale use. For this reason, the use of the corresponding sulfonates is preferred in this special case, which are readily available, for example, by reacting mixed anhydrides of aliphatic carboxylic acids and aliphatic or aromatic sulfonic acids (M. H. Karger et al., J. Org. Chem. 36 (1971), pp. 528-531) with the formaldehyde dialkyl acetals or dialkoxyalkyl acetals in a smooth and nearly quantitative reaction (M. H. Karger et al., J. Amer. Chem. Soc. 91 (1969), pp. 5663/5665:

$R_9$—$SO_2$—O—CO—$(C_1-C_4)$Alkyl +

$R_{10}$—O—$CH_2$—O—$R_{10}$ — $(C_1-C_4)$Alkyl-$CO_2R_{10}$ ⟶

$R_9$—$SO_2$—O—$CH_2$—O—$R_{10}$

In this equation, $R_9$ represents an aliphatic group such as methyl, ethyl, or trifluoromethyl, or an aromatic group, for example, phenyl, 4-tolyl, or 4-bromophenyl, but preferably methyl or 4-tolyl, and $R_{10}$ represents an alkyl or alkoxyalkyl group falling under the definition of $R_7$ or $R_{15}$.

The reaction can be carried out either in the substance or in an anhydrous aprotic solvent inert to the reactants at temperatures between $-20°$ and $+40°$ C., preferably between 0° and 20° C. No intermediate isolation of the highly reactive sulfonates, which are sensitive to hydrolysis and thermally labile, is necessary; they are preferably used immediately as crude products for the substitution on the nitrogen of the xanthines, with the usual addition of a basic condensing agent being unnecessary.

The reaction of the mono- or disubstituted xanthine derivatives (IX), (XVI), (VII), (XII) and (XIV) with the alkylating agent involved of formula (VIII) or (Xa) or (XIII) is ordinarily done in a distributing agent or solvent inert to the reactants. Practical representatives are especially dipolar, aprotic solvents, for example formamide, dimethylformamide, dimethylacetamide, N-methylpyrrolidone, tetramethylurea, hexamethylphosphoric triamide, dimethylsulfoxide, acetone, or butanone; however, alcohols such as methanol, ethylene glycol, and their mono- or dialkyl ethers with the alkyl group having 1 to 4 carbon atoms but both together having a maximum of 5 carbon atoms, ethanol, propanol, isopropanol, and the various butanols; hydrocarbons such as benzene, toluene, or xylenes; halogenated hydrocarbons such as dichloromethane or chloroform; pyridine, and mixtures of the solvents mentioned or their mixtures with water can also be used.

The "alkylation reactions" are suitably carried out in the presence of a basic condensing agent. Examples of materials suitable for this are alkali metal or alkaline earth hydroxides, carbonates, hydrides, alcoholates, and organic bases, such as trialkylamines (for example, triethyl- or tributylamine), quaternary ammonium or phosphonium hydroxides and crosslinked resins with fixed, optionally substituted ammonium or phosphonium groups. The xanthine derivatives can also be used in the alkylation reaction directly in the form of their separately prepared salts, such as the alkali metal, alkaline earth, or optionally substituted ammonium phosphonium salts. The mono- and disubstituted xanthine derivatives can also be alkylated either in the presence of the aforementioned inorganic condensing agents or in the form of their alkali metal or alkaline earth salts with the assistance of so-called phase transfer catalysts, for example tertiary amines, quaternary ammonium or phosphonium salts, or crown ethers, preferably in a 2-phase system under the conditions of phase transfer catalysts. Among the suitable phase transfer catalysts that are generally commercially available are tetra($C_1-C_4$)alkyl- and metyltrimethylammonium and -phosphonium salts, methyl-, myristyl-, phenyl-, and benzyltri($C_1-C_4$)alkyl- and cetyltrimethylammonium as well as ($C_1-C_{12}$)alkyl- and benzyltriphenylphosphonium salts with the compounds that have the larger and more symmetrically structured cation generally proving to be the more effective.

The introduction of the groups I

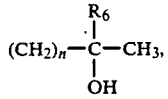

$R_7$ and $R_{15}$ by the procedures described above is generally carried out at a reaction temperature between 0° C. and the boiling point of the particular reaction medium used, preferably between 20° and 130° C., optionally at elevated or reduced pressure, for which the reaction time can amount to less than 1 hour or up to several hours.

The reaction of the 3-alkylxanthines (VIII) to produce the compounds pursuant to the invention of formula (X) requires the introduction of two tertiary hydroxyalkyl groups. Either identical or different substituents can be linked to the xanthine skeleton in succession, or two identical hydroxyalkyl groups can be linked without isolation of intermediates in a single-pot reaction.

The reductive cleavage of the benzyl and diphenylmethyl group from compounds of formula (XV) with the formation of the xanthine atom in the 7-position, is carried out under standard conditions that were developed especially in the framework of the protective group technique in alkaloid and peptide syntheses and can thus be assumed to be widely known. Besides the chemical reduction, particularly of the benzyl compounds with sodium in liquid ammonia (Houben-Weyl, Vol. XI/I (1957), pp. 974-975), the elimination of the two aforementioned aralkyl groups by catalytic hydrogenolysis using a precious metal catalyst is also especially practical (Houben-Weyl, Vol. XI/I (1957), pp. 968-971 and Vol. IV/Ic, Part I (1980), pp. 400-404. A lower alcohol is ordinarily used here as the reaction medium (optionally with the addition of formic acid or ammonia), or an aprotic solvent such as dimethylformamide or particularly glacial acetic acid; however, their mixtures with water can also be used. Especially suitable hydrogenation catalysts are palladium black and palladium on activated charcoal or barium sulfate, while other precious metals such as platinum, rhodium, and ruthenium frequently give rise to side reactions because of competitive ring hydrogenation and are therefore only conditionally usable. The hydrogenolysis is preferably carried out at temperatures between 20° C. and 100° C. and at atmospheric pressure, or preferably slight excess pressure up to approximately 10 bar, with reaction times of a few minutes to several hours generally being needed.

The 1,3,7-tri-substituted xanthines of formula (XV) that have an alkoxymethyl or alkoxyalkoxymethyl group in the position of $R_{15}$ represent O,N-acetals. Consequently, their substituents in the 7-position can be split off under the usual conditions of acid hydrolysis (cf. Houben-Weyl, Vol. VI/Ib (1984), pp. 741-745), with the 7H compounds of formula (XVI) likewise being formed. Examples of preferred groups that can be eliminated hydrolytically are the methoxy, ethoxy, and propoxymethyl groups as well as the methoxyethoxy- and ethoxyethoxymethyl groups. The reaction is advantageously carried out with heating in dilute mineral acids such as hydrochloric or sulfuric acid, optionally with the addition of glacial acetic acid, dioxane, tetrahydrofuran, or a lower alcohol, as a solution promoter. Also useful are perchloric acid or organic acids such as trifloroacetic, formic, and acetic acid, in combination with catalytic amounts of mineral acids. The alkoxyallkoxymethyl compounds in particular can also be cleaved by using Lewis acids such as zinc bromide nd titanium tetrachloride in anhydrous medium, preferably in dichloromethane or chloroform with the 7-bromoethyl or 7-bromozinc derivatives formed as intermediates hydrolyzing spontaneously during the aqueous workup. In the cleavage in mineral acid solution, the reaction temperature must be chosen so that no significant dehydration of the tertiary hydroxyalkyl group in the 1-position occurs; it should therefore be below 100° C. as a rule.

The reduction of the xanthines of formulas (XI) and (XV) with an oxoalkyl group in the position of $R_7$ or $R_{15}$ to the corresponding hydroxyalkyl compounds can indeed take place in principle either with base metals or by catalytic hydrogenation, but the method of choice consists of the reaction occurring under the very mild conditions and in high yields with simple metal hydrides ($MH_n$), complex metal hydrides ($M^1[M^2H_n]_m$), or organometallic hydrides (Houben-Weyl, Vol. IV/Id (1981). pp. 267-282, and Vol. VI/Ib. (1984), pp. 141-155). Of the numerous complex metal hydrides that can be used for the reduction of ketones, the most frequently used reagents might be mentioned, for example, lithium alanate, lithium borohydride, and especially sodium borohydride, that is easier to handle because of its lower reactivity and above all permits working in alcoholic, alcoholic aqueous, and pure aqueous solutions or suspensions. In addition to the otherwise customary inert solvents such as ethers (for example, diethyl ether, tetrahydrofuran, 1,2-dimethoxyethane), hydrocarbons and pyridine, nitriles such as acetonitrile can also be used as the reaction medium. The hydrogenation, which is suitablly carried out at temperatures between 0° C. and the boiling point of the particular solvent, but preferably at room temperature, generally occurs rapidly and is complete within several minutes to a few hours.

The tertiary hydroxyalkylxanthines of formula (II) can also be prepared by reacting substituted xanthines of formula (XIX)

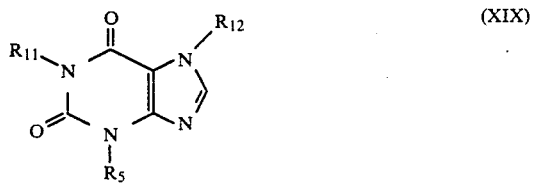

e) contain two identical or different groups of the formula $$-(CH_2)_n-CO-CH_3 \qquad (XX);$$

or $$-(CH_2)-_n-CO-R_6 \qquad (XXI),$$

or only one substituent of the formula (XX) or (XXI), and hydrogen or the group $R_7$ or $R_{15}$ in the positions of $R_{11}$ and $R_{12}$, with ($C_1$-$C_3$)alkyl- or methylmetal compounds with reductive "alkylation" of the carbonyl groups to obtain the xanthines pursuant to the invention of formulas (IX) to (XVI), or f) metallating xanthines of formula (XIX) that have two identical or different groups of the formula $-(CH_2)_n$—Hal (XVII), with Hal preferably standing for chlorine or bromine, or only one such group and hydrogen or the substituent $R_7$ or $R_{15}$ in the other position, in the terminal position, and then reacting them with the ketones of the formula $$R_6-CO-CH_3 \qquad (XVIII)$$

with reductive alkylation of the carbonyl group to obtain the xanthines of formulas (IX) to (XVI) pursuant to the invention, or g) converting xanthines of formula (XIX) with the group $$-(CH_2)_n-COO-(C_1-C_4)alkyl \qquad (XXIV)$$

in the positions of $R_{11}$ and/or $R_{12}$ and optionally hydrogen or the group $R_7$ or $R_{15}$ in the other position, by means of two equivalents of a methylmetal compound per alkoxycarbonyl group, into xanthines of formulas (IX) to (XVI) in which $R_7$ stands for methyl, or h) converting xanthines of formulas (XIX) having two identical or different groups of the formula

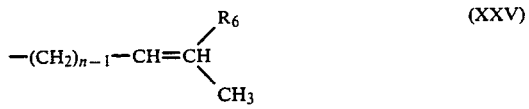

or only one such group and hydrogen or the group $R_7$ or $R_{15}$ in the positions of $R_{11}$ and $R_{12}$, in which the group (XXV) can contain the C=C double bond also in position-isomeric arrangements on the branched carbon atom, for example, as —C=CH$_2$, by acid-catalyzed hydration obeying the Markownikoff Rule, into the xanthines of formulas (IX) to (XVI) pursuant to the invention, and if desired, then converting the tertiary hydroxyalkylxanthines of formulas Ib' and if obtained pursuant to the invention by methods e) to h) that have a hydrogen atom in the 1- or 7-position, optionally in the presence of basic media or in the form of their salts, with the alkylating agents of formula (VIII) or (Xa) or (XIII), into the trisubstituted compounds of formulas (X) or (XI) or (XV) in which $R_5$, $R_6$, $R_7$, $R_{15}$, and n in the formulas above have the meanings indicated above.

The 3-alkylated mono- or dioxoalkyl- (XIXa), -(ω-haloalkyl) (XIXb), -(ω-alkoxycarbonylalkyl)- (XIXc), and -alkenylxanthines (XIXd) needed for this as starting materials are either known or can be prepared readily, for example, from the 3-alkyl-xanthines (VII) and the sulfonyloxy- or haloketones (XVII) and (XVIII), ω-haloalkylsulfonates, or 1,ω-dihaloalkanes (cf., for example: V. B. Kalcheva et al., Journal fur prakt. Chemie 327 (1985) pp. 165-168), ω-sulfonyloxy or ω-halocarboxylic acid alkyl esters or sulfonyloxy or haloalkenes corresponding to formula (XXV) under the reaction conditions previously described in detail for the alkylation of mono- and disubstituted xanthines with the compounds of formulas (VIII) and (Xa).

In the organometallic reactions of the xanthines (XIXa) and (XIXc) functionalized in the $R_{11}$ and $R_{12}$ groups, the procedure is the same in principle as described for the preparation of the tertiary alcohols of formula (VIII) used as alkylating agents. Thus, the reductive alkylation of the ketones (XIXa) and of the esters (XIXc) can take place, for example, with alkylpotassium, -sodium, -lithium, -magnesium, -zinc, -cadmium, -aluminum, and -tin compounds. The recently recommended alkyltitanium and -zirconium compounds (D. Seebach et al., Agnew. Chem. 95 (1983) pp. 12–26) can also be used. However, since the alkylmetal compounds of sodium and potassium have a tendency toward side reactions because of their high reactivity and those of zinc and cadmium are relatively sluggish, the alkyllithium and -magnesium (Grignard) compounds are ordinarily preferred.

The strong nucleophilic organometallic compounds are very sensitive to hydrolysis and oxidation. Their safe handling therefore requires working in anhydrous medium, optionally under an inert gas atmosphere. The usual solvents or distributing agents are primarily those that are suitable also for the preparation of the alkylmetal compounds. Practical examples are especially ethers with one or more oxygen atoms, for example diethyl, dipropyl, dibutyl, or diisoamyl ether, 1,2-dimethoxyethane, tetrahydrofuran, dioxane, tetrahydropyran, furan, and anisole, and aliphatic or aromatic hydrocarbons such as petroleum ether, cyclohexane, benzene, toluene, xylene, diethylbenzene and tetrahydronaphthalene; however, tertiary amines such as triethylamine, or dipolar aprotic solvents such as hexamethylphosphoric triamide, as well as mixtures of the solvents mentioned can also be used successfully. The reaction of the carbonyl compounds (XXXIXa) and (XIXc) with the Grignard compounds with the formula $R_6$-MgHal can also beneficially be carried out by placing the organometallic compound in an ether and adding the ketone or the ester dropwise as a solution in dichloromethane or 1,2-dichloromethane. An addition of magnesium bromide is frequently recommended, which is able to increase the nucleophilicity of the organometallic compound because of its participation in the complex cyclic transition state.

The ketone or ester and the organometallic compound are generally combined at temperatures between $-26°$ C. and 100° C., preferably between 0° C. and 60° C., or at room temperature without external cooling, with the alkylmetal compound ordinarily being used in slight excess. The reaction is then ordinarily completed by brief heating under reflux, for which times of several minutes to a few hours are generally adequate. The alkanolate formed is preferably decomposed with aqueous ammonium chloride solution or dilute acetic acid.

Metallic magnesium and lithium are primarily suitable for the metallation of the ω-haloalkylxanthines (XIXb). On the other hand, the replacement of the halogen atom with lithium which is also possible using organolithium reagents, generally 1-butyl-, 2-butyl-, t-butyl-, or phenyllithium, plays a subordinate role. However, use is made especially of the Grignard compounds, advantageously preparing them in the ethers, hydrocarbons, tertiary amines, or aprotic solvents listed as particularly suitable for the reaction of the xanthines (XIXa) and (XIXc) with alkylmetal compounds, at temperatures between 25° and 125° C., preferably below 100° C. If the metallation reaction is carried out in hydrocarbons, then the addition of an ether such as tetrahydrofuran, or a tertiary amine such as triethylamine in stoichiometric amount frequently proves useful. The use of catalysts such as butanol, aluminum chloride, silicon tetrachloride, tetrachloromethane, and aluminum or magnesium alcoholates may also be helpful. In the halogen-metal exchange the chlorides ordinarily react more slowly than the corresponding bromides and iodides, but as a rule the provide better yields of organometallic compound. To accelerate the beginning of the rection, the addition of some magnesium bromide, some grams of iodine, or several drops of bromine, tetrachloromethane, or methyl iodide with slight heating is frequently recommended. The Grignard compounds obtained are normally not isolated, but are reacted immediately with the ketones of formula (XXIII) under the reaction conditions described for the reductive alkylation of the xanthines (XIXa) and (XIXc).

The addition of water to the C=C double bond of the alkenylxanthines (XIXd) with the structural element of formula (XXV), in which the hydroxy group adds to the carbon atom with the fewer hydrogens to form tertiary alcohols according to the Markownikoff Rule, ordinarily occurs in aqueous solution or suspension in the presence of strong acids such as sulfuric, nitric or phosphoric acid. Hydrogen halides and sulfonic acids such as trifluoromethanesulfonic acid, acid exchange resins, boron trifluoride complexes, or oxalic acid can also be used as catalysts. However, it is preferred to operate in sulfuric acid, with an acid concentration of 50 to 65% and temperatures of 0° to 10° C. being sufficient as a rule. However, lower or higher acid concentration and/or reaction temperatures can sometimes also be used. In any case, the reaction temperatures should be kept as low as possible since the reverse dehydration to the olefin can be disturbingly significant above approximately 60° C.

The addition of a solvent inert to acids such as 1,4-dioxane, benzene, or toluene sometimes also provides benefits. Since esters can form as intermediates in the acid-catalyzed hydration, particularly when using the high acid concentrations, it is recommended to treat the reaction batch with a large amount of water with brief heating after the action of the acid for the purpose of ester hydrolysis, or to process the mixture in the alkaline range.

The experimental conditions for the optional conversion of the 1- and 7H-compounds (IX) or (XVI) pursuant to the invention into the trisubstituted xanthines of formulas (X) or (XI) or (XV) by N-alkylation with the compounds (VIII) or (Xa) of (XIII) have already been described above in detail.

Depending on the chain length of the alkyl group $R_6$ (at least $C_2$) and/or the structure of a substituent $R_7$ (for example, 2-hydroxypropyl), the tertiary hydroxyalkylxanthines of formula (II) can have one or two asymmetric carbon atoms and can thus be present in stereoisomeric forms. This invention therefore concerns both the pure stereoisomeric compounds and their mixtures.

The compounds I and II or a suitable mixture thereof are effective in substantially reducing the nephrotoxicity induced by the aminoglycoside, e.g. tobramicin, amicasin, gentamicin, etc., at a relatively low concentration, e.g. typically about 50 mg of xanthine per kg of body weight of the host being treated. The demonstrated inhibition or reduction of nephrotoxicity by the compounds of the instant invention is, of course, suggestive of clinical effectiveness in substantially reducing the nephrotoxicity in a host treated with an aminoglycoside inducing such nephrotoxicity. Appropriate dosages will vary with the condition and the individual being treated.

Effective amounts of the xanthines can be administered to a subject by any one of various methods, for example, orally as in capsule or tablets, or parenterally in the form of sterile solutions. The xanthines, while effective themselves, can be formulated and administered in the form of their pharmaceutically acceptable addition salts for purposes of stability, convenience of crystallization, increased solubility, and the like.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaic acid, oxalic acid, and the like; and salts of tribasic carboxylic acids, such as carboxysuccinic acid, citric acid, and the like.

The xanthines can be administered orally, for example, with an inert diluent or with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, wafers, chewing gums, and the like. These preparations should contain at least 0.5% of active compound, but the amount can be varied depending upon the particular form and can conveniently be between 4.0% to about 70% of the weight of the unit. The amount of xanthine in such compositions is such that a suitable dosage will be obtained. Preferred compositions and preparations according to the present invention are prepared so that an oral dosage unit form contains between about 1.0 mgs and about 300 mgs of active compound.

Tablets, pills, capsules, troches, and the like can contain the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotex; a glidant, such as colloidal silicon dioxide; a sweetening agent, such as sucrose or saccharin; or flavoring agent, such as peppermint, methyl salicylate, or orange flavoring. When the dosage unit form is a capsule, it can contain, in addition to material of the above type, a liquid carrier, such as a fatty oil.

Other dosage unit forms can contain other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings and flavors. Materials used in preparing these compositions should be pharmaceutically pure and non-toxic in the amounts used.

For purposes of parenteral therapeutic administration, the xanthines can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 0.5 mg to 100 mgs of the active compound.

Solutions or suspensions of the xanthines can also include the following components: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

While dosage values will vary with the nephrotoxic condition to be alleviated, good results are achieved when the xanthines of formula (I) or formula (II) or suitable mixtures thereof are administered to a subject requiring such treatment at an effective oral, parenteral or intravenous dose in excess of 10 mg/kg of body weight per day. A particularly preferred effective amount is about 50 to 100 mg/kg of body weight per day. In general, daily dosages will vary from in excess of 10 to 1,000 mg, preferably 100–600 mg per day.

It is to be understood, however, that for any particular subject, specific dosage regimens should be adjusted to the individual need and the professional judgement of the person administering or supervising the administration of the xanthines. It is to be further understood that the dosages set forth herein are exemplary only and that they do not, to any extent limit the scope or practice of the invention.

This invention will now be described in greater detail in the following Examples.

EXAMPLE

Male rats, Sprague Dawley (175 gm), were given, subcutaneously, 60 mg/kg doses of gentamicin for 7 days. A set of rats was selected and subcutaneously administered HWA448 at 50 mg/kg and 100 mg/kg doses twice daily at the same time as the gentamicin administration. The HWA448 dosages were made up in saline. On the eighth day, the rats were anesthetized and their kidneys were removed and (1) were examined for bound urea nitrogen (BUN), a standard measurement for nephrotoxicity, and (2) were histologically examined. Presented below in the table are the results which indicate that HWA448 is effective in inhibiting or protecting against nephrotoxicity induced by the gentamicin.

TABLE

|  | BUN (mg/dl) | Histologic Damage* |
|---|---|---|
| Control (saline, s.c.) | 15.9 ± 1.4 | 0 |
| Gentamicin ("G") | 62.2 ± 11.9+ | 2.8 |
| G + HWA448 (100 mg/kg) | 25.0 ± 3.1 | 1.8 |
| G + HWA (50 mg/kg) | 31.1 ± 1.5 | 2.0 |
| G + HWA (10 mg/kg) | 41.5 ± 5.6 | 2.2 |

*Scale:
0 = normal
1 = mild
2 = moderate
3 = severe

What is claimed is:

1. An aminoglycoside composition having reduced nephrotoxicity, which comprises:

in addition to the aminoglycoside an effective amount of a compound selected from the group consisting of (a) at least one 7-(oxoalkyl)1,3-dialkyl xanthine of the formula

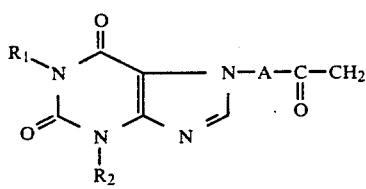

in which each of $R_1$ and $R_2$ is the same or different and is independently selected from the group consisting of straight-chain or branched alkyl radicals with 2 to 6 carbon atoms, cyclohexyl, straight-chain or branched chain alkoxyalkyl and hydroxyalkyl radicals; and A is a hydrocarbon radical with up to 4 carbon atoms which can be substituted by a methyl group; (b) a tertiary hydroxyalkylxanthine of the formula

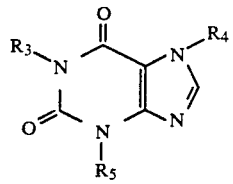

wherein at least one of $R_3$ and $R_4$ is a tertiary hydroxyalkyl group of the formula

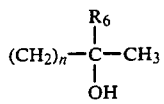

in which $R_6$ is an alkyl group with 1 to 3 carbon atoms and n stands for a whole number from 2 to 5, the other $R_3$ or $R_4$ group that may optionally be present is a hydrogen atom or an aliphatic hydrocarbon group $R_7$ having up to 6 carbon atoms, whose carbon chain may be interrupted by up to 2 oxygen atoms or may be substituted with an oxo group or up to two hydroxyl groups and $R_2$ is an alkyl group with 1 to 4 carbon atoms; and (c) a mixture of the foregoing compounds.

2. The composition as defined in claim 1 wherein said aminoglycoside is selected from the group consisting of gentamicin, amikacin, a kanamycin, neomycin, netilimicin, streptomycin, a nembramycin and a mixture of the foregoing.

3. The composition as defined in claim 2 wherein said aminoglycoside is gentamicin.

4. The composition as defined in claim 1 wherein said compound (a) is selected from the group consisting of (a') 1,3-di-n-butyl-7-(2-oxopropyl)xanthine, (b') 7-(3-oxobutyl)-1,3-di-n-butyl xanthine and (c') a suitable mixture of the foregoing.

5. The composition as defined in claim 4 wherein said aminoglycoside is gentamicin.

6. The composition as defined in claim 1 wherein said compound (b) is selected from the group consisting of (a') said compound (b) where $R_3$ is

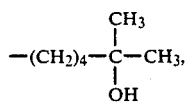

$R_4$ is $-CH_2OCH_2CH_3$ and $R_5$ is $CH_3$, (b') said compound (b) where $R_3$ is

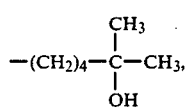

$R_4$ is H and $R_5$ is $CH_3$ and (c') a suitable mixture of the foregoing.

7. The composition as defined in claim 6 wherein said aminoglycoside is gentamicin.

8. The composition as defined in claim 7 wherein said compound (b) is (a').

9. A method of reducing nephrotoxicity in a host which has been treated with an aminoglycoside which induces the nephrotoxicity, which comprises:

administering to the host an effective amount of a compound selected from the group consisting of
(a) at least one 7-(oxoalkyl)1,3-dialkyl xanthine of the formula

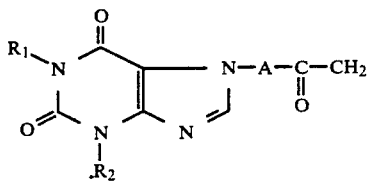
(I)

in which each of $R_1$ and $R_2$ is the same or different and is independently selected from the group consisting of straight-chain or branched alkyl radicals with 2 to 6 carbon atoms, cyclohexyl, straight-chain or branched chain alkoxyalkyl and hydroxyalkyl radicals; and A is a hydrocarbon radical with up to 4 carbon atoms which can be substituted by a methyl group; (b) a tertiary hydroxyalkylxanthine of the formula

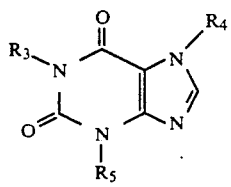
(II)

wherein at least one of $R_3$ and $R_4$ is a tertiary hydroxyalkyl group of the formula

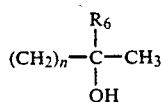

in which $R_6$ stands for the alkyl group with 1 to 3 carbon atoms and n stands for a whole number from 2 to 5, the other $R_3$ or $R_4$ group that may optionally be present is a hydrogen atom or an aliphatic hydrocarbon group $R_7$ with up to 6 carbon atoms, whose carbon chain may be interrupted by up to 2 oxygen atoms or may be substituted with an oxo group or up to two hydroxyl groups and $R_2$ is an alkyl group with 1 to 4 carbon atoms; and (c) a mixture of the foregoing compounds.

10. The method as defined in claim 9 wherein the host is one who has been treated with an aminoglycoside selected from the group consisting of gentamicin, amikacin, a kanamycin, neomycin, netilimicin, streptomycin, a nemromycin and a mixture of the foregoing.

11. The method as defined in claim 10 wherein said aminoglycoside is gentamicin.

12. The method as defined in claim 9 wherein said compound (a) is selected from the group consisting of (a') 1,3-di-n-butyl-7-(2-oxopropyl)xanthine, (b') 1,3-di-n-butyl-7-(3-oxobutyl)xanthine and (c') a suitable mixture of the foregoing.

13. The method as defined in claim 12 wherein the host is treated with gentamicin.

14. The method as defined in claim 9 wherein said compound (b) is selected from the group consisting of (a') said compound (b) where $R_3$ is

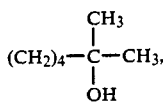

$R_4$ is $—CH_2OCH_2CH_3$ and $R_5$ is $CH_3$ (b') said compound (b) where $R_3$ is

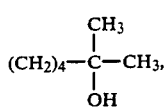

$R_4$ is H and $R_5$ is $CH_3$ and (c') a suitable mixture of the foregoing.

15. The method as defined in claim 14 wherein the host is treated with gentamicin.

16. The method as defined in claim 15 wherein said compound (b) is (a').

17. A method of reducing the nephrotoxic effect of an aminoglycoside which induces such nephrotoxic effect in a mammal treated therewith, which comprises:
administering to said mammal an effective amount of a compound selected from the group consisting of
(a) at least one 7-(oxoalkyl)1,3-dialkyl xanthine of the formula

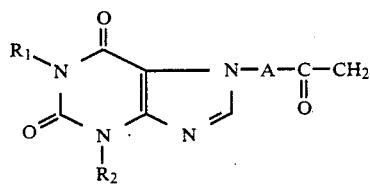
(I)

in which each of $R_1$ and $R_2$ is independently selected from the group consisting of straight-chain or branched alkyl radicals with 2 to 6 carbon atoms, cyclohexyl, straight-chain or branched chain alkoxyalkyl and hydroxyalkyl radicals; and A represents a hydrocarbon raidcal with up to 4 carbon atoms which can be substituted by a methyl group; (b) a tertiary hydroxyalkylxanthine of the formula

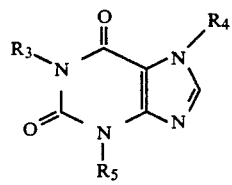
(II)

wherein at least one of $R_3$ and $R_4$ is a tertiary hydroxyalkyl group of the formula

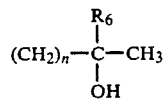

in which $R_6$ is an alkyl group with 1 to 3 carbon atoms and n stands for a whole number from 2 to 5, the other $R_3$ or $R_4$ group that may optionally be a hydrogen atom or an aliphatic hydrocarbon group $R_7$ having up to 6 carbon atoms, whose carbon chain may be interrupted by up to 2 oxygen atoms or may be substituted with an oxo group or up to two hydroxyl groups and $R_2$ is an alkyl group with 1 to 4 carbon atoms; and (c) a mixture of the foregoing compounds.

18. The method as defined in claim 17 wherein the aminoglycoside is selected from the group consisting of gentamicin, amikacin, a kanamycin, neomycin, netilimicin, streptomycin, a nemramycin and a mixture of the foregoing.

19. The method as defined in claim 18 wherein the aminoglycoside is gentamicin.

20. The method as defined in claim 17 wherein said compound (a) is selected from the group consisting of (a') 1,3-di-n-butyl-7-(2-oxopropyl)xanthine, (b') 1,3-di-n-butyl-7-(3-oxobutyl)xanthine and (c') a suitable mixture of the foregoing.

21. The method as defined in claim 20 wherein the aminoglycoside is gentamicin.

22. The method as defined in claim 17 wherein said compound (b) is selected from the group consisting of (a') said compound (b) where $R_3$ is

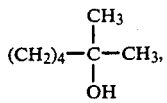

$R_4$ is —$CH_2OCH_2CH_3$ and $R_5$ is $CH_3$, (b') said compound (b) where $R_3$ is

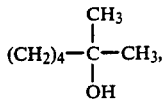

$R_4$ is H and $R_5$ is $CH_3$ and (c') a suitable mixture of the foregoing.

23. The method as defined in claim 22 wherein the aminoglycoside is gentamicin.

24. The method as defined in claim 23 wherein said compound (b) is (a').

25. The composition as defined in claim 1 which further comprises a pharmaceutically acceptable carrier.

* * * * *